United States Patent [19]

Lemaire

[11] Patent Number: 5,955,493
[45] Date of Patent: Sep. 21, 1999

[54] THIAMORPHINANS WITH NEUROPROTECTIVE ACTIVITY

[75] Inventor: Simon Lemaire, Aylmer, Canada

[73] Assignee: Biochem Pharma, Inc., Laval, Canada

[21] Appl. No.: 09/066,453

[22] PCT Filed: Oct. 30, 1996

[86] PCT No.: PCT/CA96/00728

§ 371 Date: Apr. 30, 1998

§ 102(e) Date: Apr. 30, 1998

[87] PCT Pub. No.: WO97/16183

PCT Pub. Date: May 9, 1997

[30] Foreign Application Priority Data

Oct. 30, 1995 [GB] United Kingdom ............. 9522176

[51] Int. Cl.$^6$ .................... A61K 31/38; C07D 335/04
[52] U.S. Cl. .................. 514/432; 549/24; 549/25
[58] Field of Search ............ 549/24, 25; 514/432

[56] References Cited

U.S. PATENT DOCUMENTS

| | | | |
|---|---|---|---|
| 4,806,543 | 2/1989 | Choi et al. | 514/464 |
| 5,177,218 | 1/1993 | Fischer et al. | 549/25 |
| 5,219,861 | 6/1993 | Kanematsu et al. | 514/282 |

FOREIGN PATENT DOCUMENTS

| | | |
|---|---|---|
| 0 270 290 | 6/1988 | European Pat. Off. |
| 0 612 730 | 8/1994 | European Pat. Off. |

OTHER PUBLICATIONS

Sauter et al., "Thiamorphinans I" *XP 000644576* pp. 1477–1480 (1983).

Lemaire et al., "Agonist and antagonist opioid activity of axial and equatorial conformations of S–methyl–and S–allyl–morphinans" *XP 000645102 European Journal Pharmacology* 258:111–118 (1994).

Farooqui et al., "Excitatory amino acid receptors, neural membrane phospholipid metabolism and neurological disorders" *Brain Research Reviews* 16:171–191 (1991).

MacDermott et al., "Receptors, ion channels and synaptic potentials underlying the integrative actions of excitatory amino acids" *TINS* 10:280–284 (1987).

Olney, "Toxic Effects of Glutamate and Related Amino Acids on the Developing Central Nervous System" pp. 501–512 (1989).

Said et al., "N–Methl–D–Aspartate Receptors Outside the Central Nervous System: Activation Causes Acute Lung Injury that is Mediated by Nitric Oxide Synthesis and Prevented by Vasoactive Intestinal Peptide" *Neuroscience* 65:943–946 (1995).

Olney, "Excitotoxic Amino Acids and Neuropsychiatric Disorders" *Ann. Rev. Pharmacol. Toxicol* 30:47–71 (1990).

Foster et al., "Therapeutic Potential of NMDA Receptor Antagonists as Neuroprotective Agents" *Current and Future Trends in Anticovulsant, Anxiety, and Stroke Therapy* pp. 301–329 (1990).

Rogawski et al., "Antiepileptic Drugs: Pharmacological Mechanisms and Clinical Efficacy with Consideration of Promising Developmental Stage Compounds" *Pharmacol. Rev.* 42:233–286 (1990).

Koek et al., "Selective Blockade of N–Methyl–D–Aspartate (NMDA)– Induced Convulsions by NMDA Antagonists and Putative Glycine Antagonists: Relationship with Phencyclidine–Like Behavioral Effects[1]" *The Journal of Pharmacology and Experimental Therapeutics* 252:349–357 (1990).

Fray et al., "An observational Method for Quantifying the Behavioural Effects of Dopamine Agonists: Contrasting Effects of d–Amphetamine and Apomorphine" *Psycopharmacology* 69:253–259 (1980).

*Primary Examiner*—Deborah C. Lambkin
*Attorney, Agent, or Firm*—Foley & Lardner

[57] ABSTRACT

The present invention relates to morphinan derivatives that are neuroprotective against excitatory amino acid (EAA) cytotoxicity. In particular, morphinan derivatives of the invention act as antagonists at the ionotropic NMDA (N-methyl-(D)-aspartic acid) receptor and are useful as protective agents against peripheral and central nervous system NMDA-receptor mediated toxicity and convulsions.

21 Claims, No Drawings

THIAMORPHINANS WITH NEUROPROTECTIVE ACTIVITY

This application is a 371 of PCT/CA96/00728 Oct. 30, 1996.

FIELD OF THE INVENTION

The present invention relates to polycyclic alkaloids, and more particularly, to S-morphinan derivatives and their use in therapy as neuroprotective and anti-convulsant agents.

BACKGROUND OF THE INVENTION

Excitatory amino acids such as L-glutamate (Glu) and L-aspartate (Asp), are major neurotransmitters in the mammalian central nervous system. Multiple acidic amino acid receptor subtypes exist for these acid amino acid neurotransmitters. For example, these include ion channel-linked receptors mediating neuronal depolarization, named after the prototypical agonists N-methyl-D-aspartate (NMDA), alpha-amino-5-methyl-4-isoxazoleproprionic acid (AMPA), kainate and a putative presynaptic stimulator, L-2-amino-4-phosphonobutyrate (L-AP4). A fifth excitatory amino acid receptor is the metabotropic receptor, linked to phosphoinositide metabolism (Farooqui and Horrocks, Brain Res. Rev. 16, 171, 1991).

NMDA receptors play a specialized role due to the unique properties of their linked ion channels and participate in various plastic neuronal events including initiation of long-term potentiation, which is a proposed substrate of learning and memory and the establishing of synaptic contacts during neuronal development. NMDA receptors are also involved in other processes such as the transmission of sensory information (MacDermott and Dale, Trends Neurosci. 10, 280, 1987).

Apart from their important physiological roles, excitatory acidic amino acids such as NMDA are also involved in pathophysiological events in the central nervous system. Abnormally low levels of glutamic acid (Glu) can compromise normal levels of excitation and cause, for example, learning and memory deficits. Excessive levels of Glu can produce toxic effects. The term "excitotoxicity" was coined by Olney (in Hyhan W. L. [ed]: "Heritage Disorders of Amino Acids Metabolism" New York: Macmillan pp. 501–512, 1989) to describe the process by which excitatory amino acids can cause neuronal cell death.

Evidence indicates that NMDA receptors exist in the peripheral tissues and that activation of these receptors may be involved in a mechanism of lung and other organ injury (Said, S. I. et al., Letters to Neuroscience, 65, 943–946, 1995). This cytotoxic process is mainly mediated by an over-stimulation of NMDA receptors and may occur in cases of cerebral stroke, cerebral ischaemia, epilepsy, Alzheimer's disease, AIDS-related dementias, traumatic brain injury and other neurodegenerative disorders (Olney, Ann. Rev. Pharmacol. Toxicol. 30: 47–71, 1990; Foster et al, in "Current and future Trends in Anticonvulsant, Anxiety and Stroke Therapy" Wiley-Liss, Inc. pp. 301–329, 1990; Rogawski and Porter, Pharmacol. Rev., 42: 223–286, 1990).

The NMDA receptor comprises several binding domains that interact with each other for proper functioning and modulation of nerve cell activity. It is theorized that the NMDA receptor forms a complex acting as a receptor-linked ion channel. Essentially, the function of the receptor is to bind NMDA or the natural amino acids, Glu or Asp, and open an associated ion channel that allows the entry of sodium ($Na^+$) and calcium ($Ca^{2+}$) into the stimulated neuron as well as the exit of potassium ($K^+$). Whereas the ion channels of other excitatory amino acid receptors (AMPA, kainate and L-AP4) are only permeable to $Na^+$ and $K^+$, the NMDA receptor channel is also permeable to $Ca^{2+}$. This feature may be of importance for the proposed role of this receptor in both short and long-term plasticity such as learning, memory and neuropathology.

Intracellular $Ca^{2+}$ is responsible for the regulation of a large variety of cellular activities (Farooqui and Horrocks, Brain Res. Rev. 16, 171; 1991). An overstimulation of brain NMDA receptors, observed in cases of anoxia, ischaemia and hypoglycemia, results in a build-up of the concentration of $Ca^{+2}$ in stimulated neurons and a cascade of intracellular events (activation of phospholipases [$PLA_2$, PLC], lipases, proteases and endonucleases) that lead to neuronal cell death (Farooqui and Horrocks, Brain Res. Rev. 16, 171; 1991).

There is therefore a need for compounds which can bind or antagonize the NMDA receptor complex or otherwise protect neurons against excitatory amino acid receptor-induced degeneration.

SUMMARY OF THE INVENTION

In one aspect, the present invention provides a method of inhibiting excitotoxicity in a mammal comprising administering to said mammal an excitotoxicity inhibiting amount of a compound of formula (I):

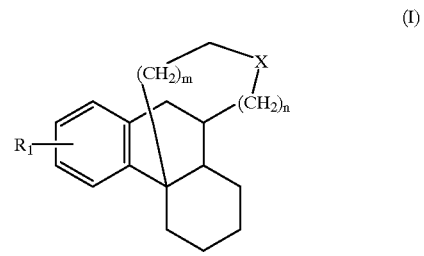

wherein $R_1$ is hydrogen, halogen, hydroxyl, $N(R_3)_2$, carboxyl, $C_{1-4}$alkyl, $C_{1-4}$alkoxy, $C_{1-4}$alkoxy-carbonyl, $C_{1-4}$acyl, $C_{1-4}$acyloxy, mercapto, $C_{1-4}$alkylthio or a saturated or unsaturated, 5 or 6-member carbocyclic or heterocyclic ring optionally substituted with halogen, hydroxyl, $N(R_3)_2$, carboxyl, $C_{1-4}$alkyl, $C_{1-4}$alkoxy or $C_{1-4}$alkoxy-carbonyl;

X is S, SO, $SO_2$ or $S^+(R_2)$;

$R_2$ is $C_{1-6}$alkyl, $C_{2-6}$alkenyl or $C_{2-6}$alkynyl groups, optionally interrupted with one or more heteroatom and optionally substituted with $R_1$;

$R_3$ is independently H or $C_{1-3}$alkyl;

m is an integer from 0 to 3; and n is an integer from 0 to 2.

In a particular embodiment there is provided a method of inhibiting convulsions in a mammal comprising administering to said mammal a convulsion inhibiting amount of a compound of formula (I) as defined above.

In another embodiment there is provided a method of inhibiting a condition in a mammal mediated by overstimulation of the NMDA-receptor complex by administering to said mammal an effective amount of a compound of formula (I) as defined above.

In another embodiment there is provided a method of inhibiting excitotoxicity in a mammal comprising administering to said mammal an excitotoxic inhibiting amount of a compound of formula (I) as defined above, wherein said excitotoxicity is mediated by the overstimulation of the NMDA receptor complex.

In another embodiment there is provided a method of inhibiting excitotoxicity in a mammal comprising administering to said mammal an excitotoxicity inhibiting amount of a compound of formula (I) as defined above, wherein said excitotoxicity is mediated by excessive in vivo levels of excitatory amino acids.

In another embodiment there is provided a method of inhibiting excitotoxicity in a mammal comprising administering to said mammal an excitotoxic inhibiting amount of a compound of formula (I) as defined above, wherein said excitotoxicity is mediated by excessive in vivo levels of NMDA or glutamic acid.

In another embodiment, compounds of formula (I) as defined above, or compositions thereof, are used in the manufacture of a medicament for use as protective agent against excitotoxicity.

According to a further aspect of the invention, there is provided novel compounds according to formula (I) with the proviso that X is not S and when $R_2$ is methyl or allyl then $R_1$ is not H, hydroxy or methoxy.

In another aspect, there is provided pharmaceutical compositions comprising compounds according to formula (I) with the proviso that X is not S and when $R_2$ is methyl or allyl then $R_1$ is not H, hydroxy or methoxy, and a pharmaceutically acceptable carrier.

DETAILED DESCRIPTION OF THE INVENTION

The following common abbreviations are used throughout the specification:
'EAA' refers to excitatory amino acid;
'NMDA' refers to N-methyl-(D)-aspartic acid;
'AMPA' refers to alpha-amino-5-methyl-4-isoxazoleproprionic acid;
'alkyl' as well as 'alkoxy', 'alkoxy-carbonyl', 'acyl', 'acyloxy' and 'alkylthio' represent saturated or unsaturated, straight or branched hydrocarbon chains;
'alkenyl' and 'alkynyl' represent unsaturated, straight or branched hydrocarbon chains.

The present invention provides a method of inhibiting excitotoxicity in mammals comprising administering to said mammal an excitotoxic inhibiting amount of a compound of formula (I) shown above.

$R_1$ may be hydrogen, halogen, hydroxyl, $N(R_3)_2$, carboxyl, $C_{1-4}$alkyl, $C_{1-4}$alkoxy, $C_{1-4}$alkoxy-carbonyl, $C_{1-4}$acyl, $C_{1-4}$acyloxy, mercapto, $C_{1-4}$alkylthio or a saturated or unsaturated, 5 or 6-member carbocyclic or heterocyclic ring optionally substituted with halogen, hydroxyl, $N(R_3)_2$, carboxyl, $C_{1-4}$alkyl, $C_{1-4}$alkoxy or $C_{1-4}$alkoxy-carbonyl.

Preferably $R_1$ is hydrogen.
Preferably $R_1$ is carboxyl.
Preferably $R_1$ is mercapto.
Most preferably $R_1$ is hydroxy.
Preferably $R_1$ is halogen such as F, Cl, Br and I.
More preferably $R_1$ is F or Cl.
Preferably $R_1$ is $C_{1-4}$alkyl such as methyl, ethyl, propyl and butyl.
More preferably $R_1$ is methyl.
Most preferably $R_1$ is $C_{1-4}$alkoxy such as methoxy, ethoxy, propyloxy and butyloxy.
More preferably $R_1$ is methoxy.
Preferably $R_1$ is $C_{1-4}$alkoxy-carbonyl such as methoxycarbonyl, ethoxy-carbonyl, propyloxycarbonyl and butyloxycarbonyl.

More preferably $R_1$ is methoxycarbonyl.
Preferably $R_1$ is $C_{1-4}$acyl such as methylcarbonyl, ethylcarbonyl and propylcarbonyl.
More preferably $R_1$ is methylcarbonyl. Preferably $R_1$ is $C_{1-4}$acyloxy such as methylcarbonyloxy, ethylcarbonyloxy and propylcarbonyloxy.
More preferably $R_1$ is methylcarbonyloxy.
Preferably $R_1$ is $C_{1-4}$alkylthio such as methylthio, ethylthio, propylthio and butylthio.
More preferably $R_1$ is methylthio.
Preferably $R_1$ is the group $(NR_3)_2$ wherein both $R_3$ are independently selected from H and $C_{1-3}$alkyl.
More preferably both $R_3$ are H.
More preferably both $R_3$ are methyl.
Preferably $R_1$ a saturated or unsaturated, 5 or 6-member carbocyclic or heterocyclic ring.
More preferably $R_1$ is a cyclohexyl or phenyl ring.
More preferably $R_1$ is a pyrrole, imidazole, piperadine, piperazine, pyridine or pyrazine ring.
$R_1$ is located at any of the positions 1–4 of the ring system (numbered according to Belleau et al, Can. J. Chem., 1986, 64:110).
Preferably $R_1$ is located at the 3-position of the ring system.

X may be S, SO, $SO_2$ or $S^+(R_2)$ wherein $R_2$ is $C_{1-6}$alkyl, $C_{2-6}$alkenyl or $C_{2-6}$alkynyl groups, optionally interrupted with one or more heteroatom and optionally substituted with $R_1$.

Preferably X is SO, $SO_2$ or $S^+(R_2)$.
More preferably X is $S^+(R_2)$.
Preferably $R_2$ is $C_{1-6}$alkyl.
More preferably $R_2$ is methyl.
More preferably $R_2$ is phenylethyl.
Preferably $R_2$ is $C_{2-6}$alkenyl.
More preferably $R_2$ is allyl.
More preferably $R_2$ is dimethylallyl.

The bridged ring containing sulfur is defined in size by m and n which are integers selected from 0 to 3 and 0 to 2 respectively. Preferably, n is 0 and m is 1–2 More preferably n is 0.
More preferably m is 1.

In particular embodiments, the compounds are conformationally resolved i.e. the equatorial (α) or axial (β) conformation with respect to the sulfur atom of the bridged ring as set out in Lemaire et al (Eur. J. Pharmacol., 1994, 258:111).

Preferably the compounds are resolved in the α conformation.

More preferably the compounds are resolved in the α conformation.

For use in the methods of the present invention, a preferred compound is 3-hydroxy-17-deaza-17-thiamorphinan 11.

For use in the methods of the present invention, a preferred compound is 3-hydroxy-17-deaza-17-allylthionium-17-thiamorphinan 12.

For use in the methods of the present invention, a preferred compound is 3-hydroxy-17-deaza-17-dimethylallylthionium-17-thiamorphinan 13.

For use in the methods of the present invention, a preferred compound is 3-hydroxy-17-deaza-17-phenethylthionium-17-thiamorphinan 14.

A preferred compound for use in methods of the present invention is 3-hydroxy-17-deaza-17-allylthionium-17-thiamorphinan 12.

A more preferred compound for use in methods of the present invention is the β conformer of 3-hydroxy-17-deaza-17-allylthionium-17-thiamorphinan 16.

A more preferred compound for use in methods of the present invention is 3-hydroxy-17-deaza-17-methylthionium-17-thiamorphinan 17.

A preferred compound of the invention is 3-hydroxy-17-deaza-17-dimethylallylthionium-17-thiamorphinan 13.

A preferred compound of the invention is 3-hydroxy-17-deaza-17-phenethylthionium-17-thiamorphinan 14.

A more preferred compound of the invention is β conformer of 3-hydroxy-17-deaza-17-allylthionium-17-thiamorphinan 16.

The compounds of the present invention bind to and block the ionotropic NMDA receptor and prevent excessive $Ca^{+2}$ entry into neurons in NMDA-receptor mediated events: a prelude to neuronal damage that follows head or spinal cord injury, strokes, and epileptic seizures; and is associated with degenerative diseases such as Alzheimer's disease, Huntington's disease, Parkinson's disease and amyotrophic lateral sclerosis; and peripheral neurotoxicity involved in lung and other organ injury. In addition, these compounds also bind to sigma receptors on presynaptic neurons and glial cells and block the excessive release of excitatory amino acids in response to neuro-pathophysiological conditions. Consequently, compounds of formula (I) are useful as neuroprotective agents in stroke, cerebral ischaemia, traumatic brain or spinal cord injury and epileptic seizures; for the management of neurodegenerative disorders such as Alzheimer's, Huntington's, and Parkinson's diseases and amytrophic lateral sclerosis (ALS).

In another embodiment, compounds of formula (I) may be modified using methods well known by those skilled in the art, to attach or otherwise incorporate radioactive isotopes such as $^{11}C$, $^{13}N$, $^{15}O$, and $^{18}F$, to enable their application as radiotracers in Positron Emission Tomography (PET). Compounds of formula (I) may also be labelled directly or via a chelating compound with radionuclide metals such as $^{99m}Tc$, $^{188}Re$ and $^{186}Re$ for use in scintigraphic imaging or with paramagnetic ions such as gadolinium, manganese or for use in Magnetic Resonance Imaging (MRI).

The preferred compounds of the present invention can be synthesized using conventional preparative steps and recovery methods known to those skilled in the art of organic and bio-organic synthesis, while providing a new and unique combination for the overall synthesis of each compound. A preferred synthetic route for intermediates and final compounds are illustrated in scheme I below.

SCHEME 1

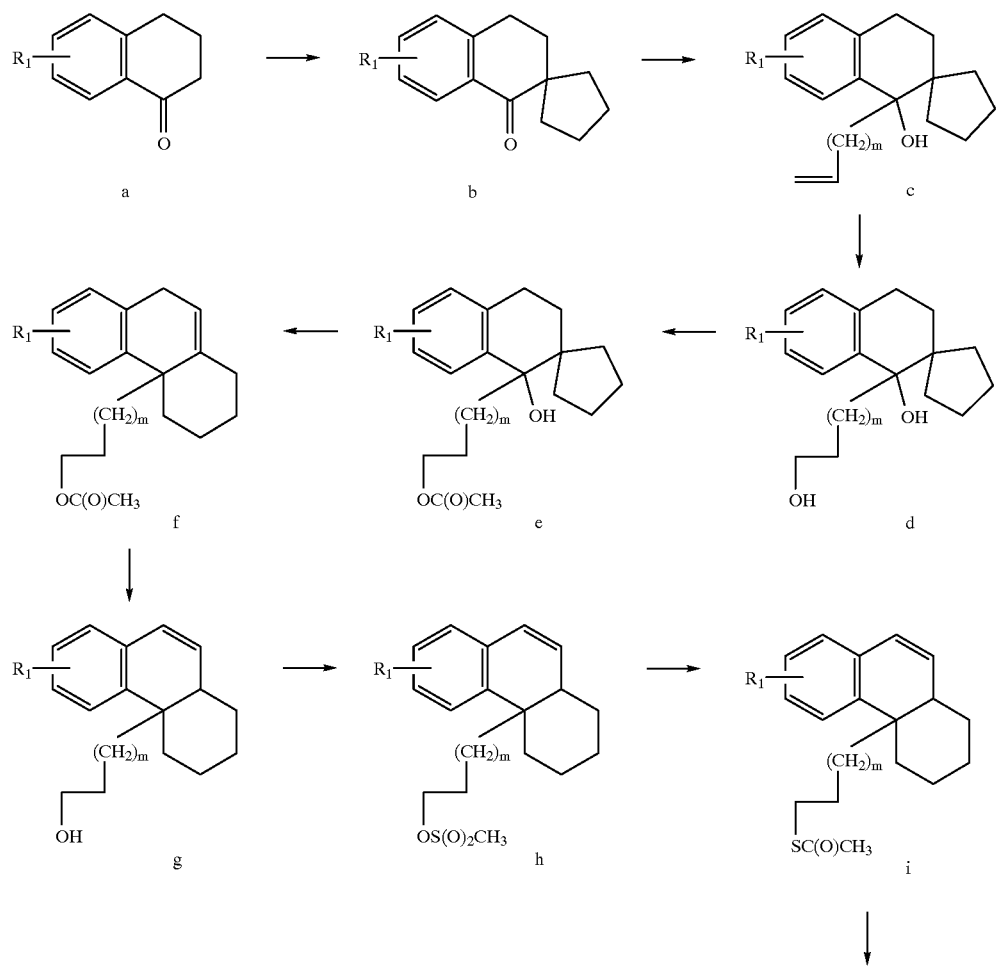

-continued

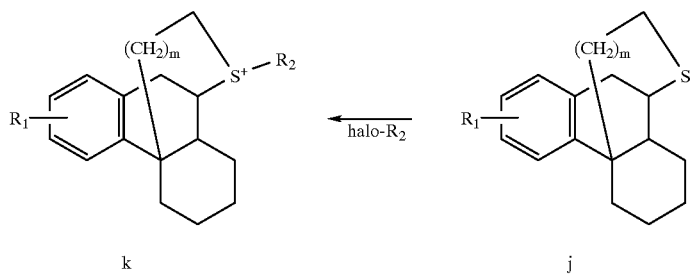

Referring to scheme I, the starting tetralone (a), obtained commercially or prepared using established synthetic techniques, is converted to the corresponding spiro intermediate (b) by reacting with 1,4-dihalo-substituted butane. This intermediate is reacted with a Grignard reagent of the general formula $CH_2=CH_2-(CH_2)_m-MgX$ to yield (c) which in turn undergoes hydroboration to yield the hydroxyl intermediate (d) followed by acetylation to give (e). Intermediate (e) is converted to the tricycle (f), which undergoes Wagner-Meerwein rearrangement (g), followed by benzylic rearrangement, mesylation (h), conversion to a thiocacetate (i), deacetylation and finally cyclization to give the S-morphinan intermediate (j). Intermediate (j) is converted to the desired final compound (k) by reacting with the desired $R_2$ group incorporating a halide substituent (i.e. $R_2$-halo). For compounds wherein X is SO or $SO_2$, intermediate (j) is oxidized with a suitable oxidizing agent such as hydrogen peroxide. Under appropriate conditions, either the sulfone or sulfoxide is produced.

Compounds of the invention wherein n is other than 0 are prepared according to established synthetic techniques. Compounds of the invention wherein n is 1, may be prepared by converting mesylated intermediate (h) to a methyl-thio intermediate followed by ionization of the methyl group and cyclization. The bridged intermediate formed is then reacted with the desired halo-$R_2$ group to give the final compound.

It is appreciated that certain $R_1$ substituents require protection during the course of the synthetic route and subsequent deprotection. For example, when $R_1$ is hydroxyl, may be converted to an alkoxy or an ester and subsequently deprotected. Protective groups for other $R_1$ substituents are described in *Protective Groups in Organic Synthesis*, 2nd ed., Greene and Wuts, John Wiley & Sons, New York, 1991.

It will be appreciated by those skilled in the art that the compounds of formula (I), depending on the substituents, may contain one or more chiral centers and thus exist in the form of many different isomers, optical isomers (i.e. enantiomers) and mixtures thereof including racemic mixtures. All such isomers, enantiomers and mixtures thereof including racemic mixtures are included within the scope of the invention. α and β conformers of the compounds are separated by conventional techniques. Generally, thionium salts or α and β mixtures are converted to their picrate derivatives and fractionally crystallized.

It is also appreciated that the compounds of the present invention can be modified by techniques established in the art in such a manner as to attach or otherwise incorporate labels such as radioactive or paramagnetic labels enabling detection of the compound for use as an imaging agent.

It is appreciated that the compounds of the present invention can be modified by one skilled in the art in such a manner as to prevent access into the central nervous system such that they can function as NMDA receptor antagonists in peripheral tissues to protect against and/or minimize cytotoxicity (neurotoxicity) involved in peripheral NMDA receptor mediated events.

The present invention also provides pharmaceutical compositions which comprise a pharmaceutically effective amount of the compounds of this invention, or pharmaceutically acceptable salts thereof, and, preferably, a pharmaceutically acceptable carrier or adjuvant. Therapeutic methods of this invention comprise the step of treating patients in a pharmaceutically acceptable manner with those compounds or compositions.

Such compositions may be in the form of tablets, capsules, caplets, powders, granules, lozenges, suppositories, reconstitutable powders, or liquid preparations, such as oral or sterile parenteral solutions or suspensions.

The therapeutic agents of the present invention may be administered alone or in combination with pharmaceutically acceptable carriers. The proportion of each carrier is determined by the solubility and chemical nature of the compound, the route of administration, and standard pharmaceutical practice.

In order to obtain consistency of administration, it is preferred that a composition of the invention is in the form of a unit dose. The unit dose presentation forms for oral administration may be tablets and capsules and may contain conventional excipients. For example, binding agents, such as acacia, gelatin, sorbitol, or polyvinylpyrolidone; fillers, such as lactose, sugar, maize-starch, calcium phosphate, sorbitol or glycine; tabletting lubricants such as magnesium stearate; disintegrants, such as starch, polyvinylpyrrolidone, sodium starch glycollate or microcrystalline cellulose; or pharmaceutically acceptable wetting agents such as sodium lauryl sulphate.

The compounds may be injected parenterally; this being intramuscularly, intravenously, or subcutaneously. For parenteral administration, the compound may be used in the form of sterile solutions containing other solutes, for example, sufficient saline or glucose to make the solution isotonic. The amount of active ingredient administered parenterally will be approximately 0.1 to 100 mg per 70 Kg person and more preferably 1 to 10 mg.

The compounds may be administered orally in the form of tablets, capsules, or granules containing suitable excipients such as starch, lactose, white sugar and the like. The compounds may be administered orally in the form of solutions which may contain coloring and/or flavoring agents. The compounds may also be administered sublingually in the form of tracheas or lozenges in which each active ingredient is mixed with sugar or corn syrups, flavoring agents and dyes, and then dehydrated sufficiently to make the mixture suitable for pressing into solid form. The amount of active ingredient administered orally will depend on bioavailability of the specific compound and is approximately 10 to 500 and more preferably 100 to 200 mg per 70 Kg person.

The solid oral compositions may be prepared by conventional methods of blending, filling, tabletting, or the like. Repeated blending operations may be used to distribute the active agent throughout those compositions employing large quantities of fillers. Such operations are, of course, conventional in the art. The tablets may be coated according to methods well known in normal pharmaceutical practice, in particular with an enteric coating.

Oral liquid preparations may be in the form of emulsions, syrups, or elixirs, or may be presented as a dry product for reconstitution with water or other suitable vehicle before use. Such liquid preparations may or may not contain conventional additives. For example suspending agents, such as sorbitol, syrup, methyl cellulose, gelatin, hydroxyethylcellulose, carboxymethylcellulose, aluminum stearate gel, or hydrogenated edible fats; emulsifying agents, such as sorbitan monooleate or acaci; non-aqueous vehicles (which may include edible oils), such as almond oil, fractionated coconut oil, oily esters selected from the group consisting of glycerine, propylene glycol, ethylene glycol, and ethyl alcohol; preservatives, for instance methyl para-hydroxybenzoate, ethyl para-hydroxybenzoate, n-propyl parahydroxybenzoate, or n-butyl parahydroxybenzoate of sorbic acid; and, if desired, conventional flavoring or coloring agents.

For parenteral administration, fluid unit dosage forms may be prepared by utilizing the peptide and a sterile vehicle, and, depending on the concentration employed, may be either suspended or dissolved in the vehicle. Once in solution, the compound may be injected and filter sterilized before filling a suitable vial or ampoule and subsequently sealing the carrier or storage package. Adjuvants, such as a local anesthetic, a preservative or a buffering agent, may be dissolved in the vehicle prior to use. Stability of the pharmaceutical composition may be enhanced by freezing the composition after filling the vial and removing the water under vacuum, (e.g., freeze drying the composition). Parenteral suspensions may be prepared in substantially the same manner, except that the peptide should be suspended in the vehicle rather than being dissolved, and, further, sterilization is not achievable by filtration. The compound may be sterilized, however, by exposing it to ethylene oxide before suspending it in the sterile vehicle. A surfactant or wetting solution may be advantageously included in the composition to facilitate uniform distribution of the compound.

The pharmaceutical compositions of this invention comprise a pharmaceutically effective amount of a compound of this invention and a pharmaceutically acceptable carrier. Typically, they contain from about 0.1% to about 99% by weight, preferably from about 10% to about 60% by weight, of a compound of this invention, depending on which method of administration is employed.

The present invention also provides a method for treatment of excitotoxicity and/or disease in patients, such as mammals, including humans, which comprises the step of administering to the patient a pharmaceutically effective amount of a compound, a pharmaceutically acceptable salt thereof, or a pharmaceutical composition as described above.

Physicians will determine the dosage of the present therapeutic agents which will be most suitable. Dosages may vary with the mode of administration and the particular compound chosen. In addition, the dosage may vary with the particular patient under treatment. The dosage of the compound used in the treatment will vary, depending on the seriousness of the disorder, the weight of the patient, the relative efficacy of the compound and the judgment of the treating physician. Such therapy may extend for several weeks, in an intermittent or uninterrupted manner, until the patient's symptoms are eliminated.

To further assist in understanding the present invention, the following non-limiting examples are provided.

EXAMPLE 1

Preparation of 3-hydroxy-17-deaza-17-thiamorphinan 11

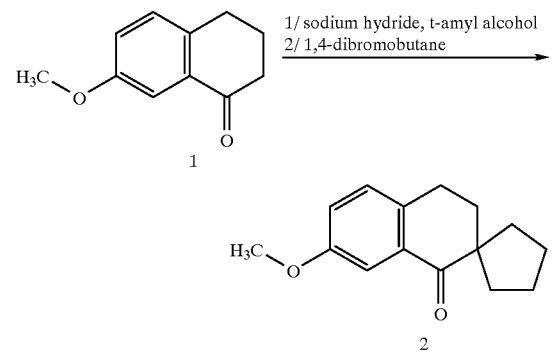

sodium hydride (8.58 g of 60% in mineral oil) was suspended in dry toluene (130 ml), put under argon and heated to 110° C. To this was added t-amyl alcohol (9.31 ml) dropwise, followed by the tetralone 1 (15 g) [source] in toluene (250 ml), and the mixture allowed to stir at reflux for 1 hour. To the hot solution was then added rapidly 1,4-dibromobutane (12.3 ml in 105 ml of dry toluene) and the mixture allowed to stir over night at 110° C. The reaction was then cooled in an ice bath, quenched slowly with isopropanol, diluted with water, washed thoroughly with brine, the organic layer dried over magnesium sulfate and evaporated in vacuo. The crude oil was purified by flash chromatography (4:1 toluene:hexane eluent) to give 2, a clear, colorless oil. Yield 90% (18.2 g).

$^1$H NMR (CDCl$_3$, 300 MHz, δ in ppm); 1.5–1.6 (2H, m), 1.63–1.85 (4H, m), 2.05 (2H, t, J=6.04), 2.06–2.16 (2H, m), 2.9 (2H, t, J=6.04), 3.8 (3H, s), 6.9–7.5 (3H, ArH).

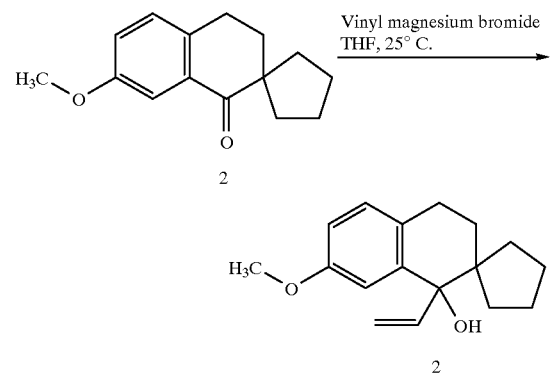

The starting ketone 2 (15 g, 65.2 mmol) was azeotroped with benzene, dissolved in THF (100 ml) and cooled to −78° C. To this was rapidly added vinyl magnesium bromide (130.4 ml of 1.0 M in THF, 2 eq). After 10 minutes, the cold bath was removed and the reaction was allowed to warm at room temperature over 2 hours. The reaction was then quenched with brine, filtered and the mother liquor extracted with ethyl acetate (3×). The combined organic layers were then dried with magnesium sulfate and evaporated in vacuo to give 3 a yellow oil (20.5 g) Yield 90%.

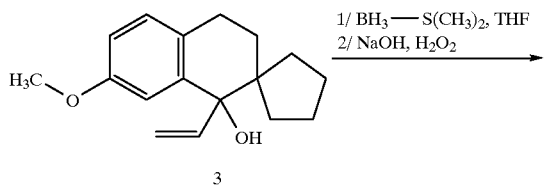

The starting alcohol 3 (2,0 g, 7.7 mmol) was azeotroped with benzene, dissolved in anhydrous THF (25 ml, freshly distilled), placed under argon and cooled to 0° C. To this was added the borane/dimethyl sulfoxide complex (77 ml of 2M soln in THF, 10 eq) and the reaction was allowed to warm at room temperature over 2 hours. The reaction was then cooled to 0° C., sodium hydroxide solution (30 ml of 5 N, 155 mmol, 20 eq) was added slowly followed immediately by hydrogen peroxide (35 ml of 30% w/w, 40 eq), and the mixture was allowed to warm at room temperature overnight. The reaction was then extracted with ethyl acetate (3×), the combined organic layers were washed with ammonium chloride (2×), brine (3×), dried over MgSO$_4$ and evaporated in vacuo to give a yellow oil (2.8 g). The crude was then purified via flash chromatography-(Merck c-60 silica gel, 5:1 hexane:ethyl acetate) to give 4, a white solid (1.8 g). Yield 73%.

$^1$H NMR (CDCl$_3$, 300 MHz, δ in ppm); 7.18 (1H, d), 6.96 (1H, m), 6.70 (1H, m), 3.80 (3H, s), 3.6 (1H, s), 3.2 (1H, s), 3.05 (1H, s), 2.6–2.9 (2H, m), 1.1–2.2 (12H, m).

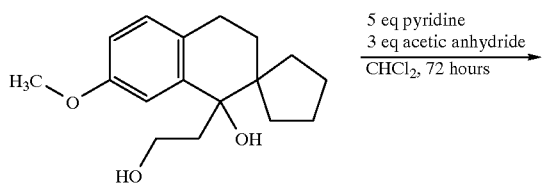

The diol 4 (7.0 g, 25.4 mmol) was azeotroped with benzene, dissolved in dichloromethane (150 ml) and cooled to 0° C. To this was added pyridine (9.53 ml, 5.0 eq), followed by acetic anhydride (7.16 ml, 3 eq) dropwise over 10 minutes. The reaction was allowed to stir for 72 hours at which time the mixture poured onto sat. sodium bicarbonate solution while cooling. More sodium bicarbonate was added until solution was basic. The layers were then separated and the aqueous phase extracted 2 times with dichloromethane. The combined organic layers were washed with sat. ammonium chloride, dried over MgSO$_4$ and evaporated in vacuo to give beige crystals (7.3 g). This was then purified by flash chromatography (2.5:1 hexane:ethyl acetate) to give 5, white crystals. Yield 88% (7.3 g).

$^1$H NMR (CDCl$_3$, 300 MHz, δ in ppm); 1.2–1.8 (8H, m), 1.95 (3H, s, AcO), 2.05–2.15 (2H, m), 2.75–2.85 (2H, m, ArCH$_2$), 3.8 (3H, s, OCH$_3$), 4.0–4.1 (1H, m), 4.2–4.3 (1H, m), 6.68–6.71 (1H, m, ArH), 6.94–6.97 (1H, m, ArH), 7.05–7.06 (1H, m, ArH).

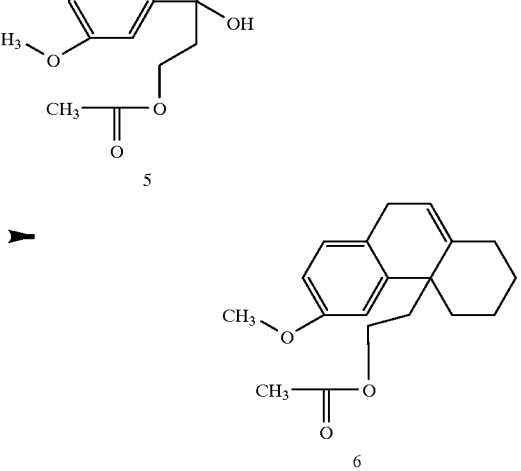

The alcohol 5 (7.0 g, 22 mmol) was azeotroped with benzene, put under argon and dissolved in dry THF (250 ml). To this was added boron trifluoride diethyl etherate (1.5 ml) and the reaction was allowed to reflux over night. The solvent was then evaporated to ⅓ its original volume, diluted with ethyl acetate, poured onto sat. sodium bicarbonate and the aqueous layer extracted with ethyl acetate (2×). The combined organic layers were then washed with brine, dried with MgSO$_4$, evaporated in vacuo and purified via flash chromatography (7:1 hexane:ethyl acetate eluent) to give 6, white crystals. Yield 69% (5.31 g).

$^1$H NMR (CDCl$_3$, 300 MHz, δ in ppm); 1.85 (3H, s, AcO), 1.1–2.2 (1OH, m), 2.25–2.34 (1H, m), 3.29 (2H, m, ArCH$^2$), 3.46–3.55 (1H, m), 3.78 (3H, s, OCH$_3$), 3.85–3.95 (1H, m) 5.6–5.7 (1H, m, vinylic), 6.6–6.97 (3H, m, ArH).

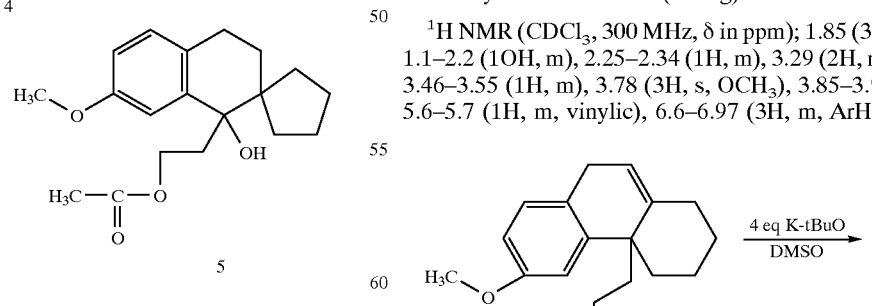

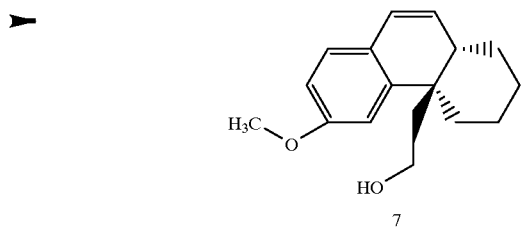

7

The acetate 6 (5.31 g) was azeotroped with benzene and dissolved in dry DMSO (100 ml). To this at room temperature was added potassium t-butoxide (4.35 g, 4.6 eq) and the mixture was allowed to stir for 5 days. The reaction was then quenched with brine and extracted with ethyl acetate (3×). The combined organic layer were then washed thoroughly with brine to remove remaining DMSO, the organic layer dried with MgSO₄ and evaporated to dryness in vacuo. The residue was then dissolved in methanol (100 ml), the solution bubbled with ammonium until saturation and let stir over night at room temperature. The solvent was then evaporated to dryness and the residue purified via flash chromatography (5:1 hexane:ethyl acetate eluent) to give 7, white crystals. Yield 55% (2.2 g).

¹H NMR (CDCl₃, 300 MHz, δ in ppm); 0.85–1.7 (8H, m), 1.99–2.17 (2H, m), 2.39–2.44 (1H, m), 3.37–3.58 (2H, m), 5.75–5.85 (1H, dd, J=9.5 Hz, J'=6.15 Hz), 6.25–6.31 (1H, dd, J=9.5 Hz, benzylic), 6.65–6.69 (1H, m, ArH), 6.78–6.83 (1H, m, ArH), 6.95–7.0 (1H, m, ArH).

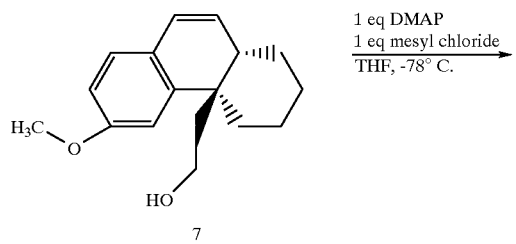

7

1 eq DMAP
1 eq mesyl chloride
THF, -78° C.

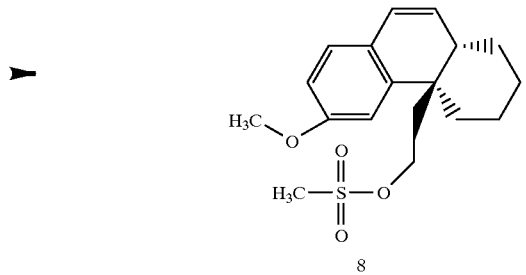

8

The alcohol 7 (3g, 11.7 mmol) was azeotroped with benzene, put under argon, dissolved in THF and cooled to −78° C. To this was added of DMAP (1.4 g, 1 eq) followed by mesyl chloride (0.9 ml, 1 eq) and the reaction was allowed to warm to room temperature over night. The reaction was then poured onto water and extracted with methylene chloride (3×). The combined organic layers were then dried with MgSO₄ and evaporated in vacuo to give 8, a yellow oil (3.9 g).

¹H NMR (CDCl₃, 300 MHz, δ in ppm); 0.9–1.75 (10H, m), 1.97–2.04 (1H, m), 2.22–2.311 (1H, m), 2.4–2.44 (1H, m), 2.85 (3H, s, CH₃SO₂), 3.80 (3H, s, OCH₃), 3.889–4.15 (2H, m), 5.83 (1H, dd, J=9.6, J'=6.15), 6.31 (1H, s, J=9.6), 6.7 (1H, m, ArH), 6.8–6.85 (1H, m, ArH).

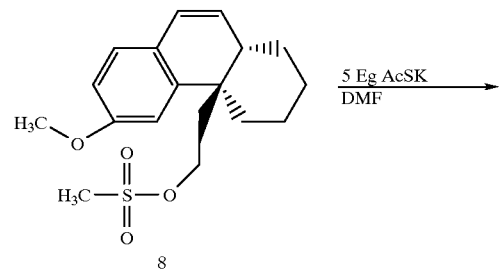

8

5 Eg AcSK
DMF

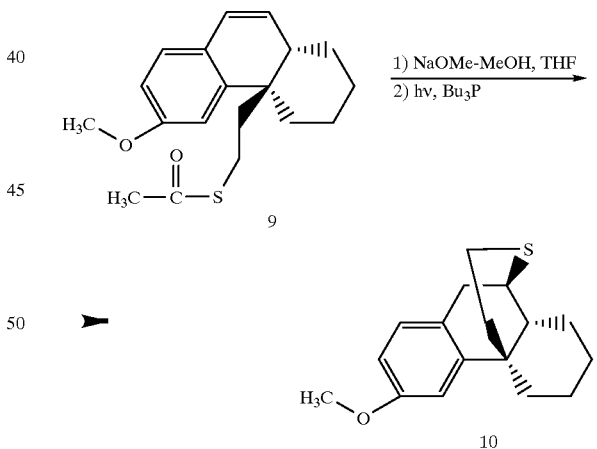

9

The mesylate 8 (3.9 g, 11.7 mmol) was azeotroped (3×) with benzene, put under argon and dissolved in DMF (150 ml). To this was added potassium thioacetate (6.7 g, 5 eq) and the reaction was allowed to stir for 72 hours. The reaction was then poured onto brine and extracted with ethyl acetate (3×). The combined organic layers were then washed thoroughly with brine, dried with magnesium sulfate and evaporated in vacuo to give a brown oil. Purification was done via flash column (9:1 toluene:hexane eluent) to give 9, a red oil. Yield 95% (3.5 g).

¹H NMR (CDCl₃, 300 MHz, δ in ppm); 0.99–1.63 (8H, m), 1.99–2.10 (2H, m), 2.26 (3H, s, AcS), 2.36–2.46 (2H, m), 2.82–2.93 1H, m), 3.82 (3H, s, CH₃O), 5.81 (1H, dd, J=9.5 Hz, J'=6.15), 6.31 (1H, d, J=9.5 Hz), 6.69–6.72 (1H, m, ArH), 6.83–6.84 (1H, m, ArH), 7.0 (1H, m, ArH).

9

1) NaOMe-MeOH, THF
2) hv, Bu₃P

10

The thioacetate 9 (3g, 10.95 nmol) was azeotroped with toluene, dissolved in dry THF (100 ml) and then degassed with argon ½hour at room temperature. To this solution was added sodium methoxide (0.5M solution, 20.9 ml) and the mixture was allowed to stir for 2 hours. The solvent was evaporated off and the residue extracted with methylene chloride, washed with aq. satd. NH₄Cl, brine respectively, dried over MgSO₄ and then evaporated. The residue was azeotroped with toluene and dissolved in dry toluene (250 ml). It was degassed with argon for ½hour and then tributylphosphine (2.37 ml, 1 eq.) was added. A water condenser was attached to the reaction flask and the contents were photolysed with sun lamp for 3 days under argon atmosphere. The solvent was evaporated off and the residue was purified on a silica gel column using a mixture of hexane and toluene (2:1, 1:1, 1:1.5 respectively). The product 10, a clear oil (1.5 g, 55% yield), was allowed to crystallize from hexane.

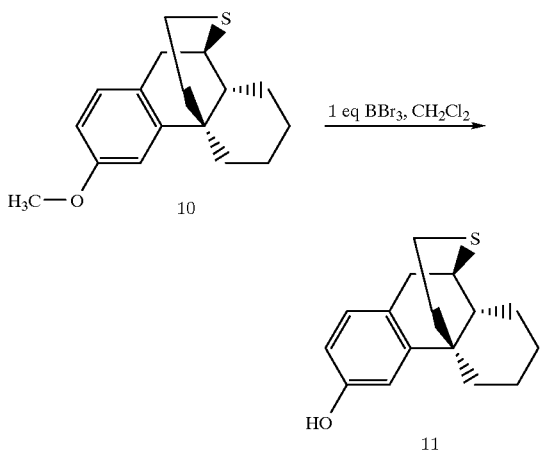

The sulfide 10 (1.21 g, 3.82 mmol) was azeotroped with toluene, dissolved in dry methylene chloride (40 ml) and cooled to −78° C. To this was added of BBr₃ (5.3 ml, 1.36 eq) and the reaction was allowed to warm to room temperature and stirred for 96 hours. The reaction was then cooled to 0° C., methanol (5 ml) was added and the solution allowed to stir at room temperature for 1 hour. The solvent was then evaporated to dryness, the residue re-dissolved in diethyl ether, washed with sat. sodium bicarbonate solution and the aqueous layer extracted with diethyl ether (3×). The combined organic extracts were then dried over magnesium sulfate, evaporated in vacuo and purified via flash chromatography (chloroform eluent) to give a yellow oil (0.74 g). This was then crystallized from hot methylene chloride to give 11, white crystals. Yield 60% (0.6 g).

¹H NMR (CDCl₃, 300 MHz, δ in ppm); 1.16–1.52 (6H, m), 1.63–1.73 (3H, m), 1.80–1.87 (1H, m), 2.10–2.23 (3H, m), 2.54–2.73 (3H, m), 2.54–2.73 (1H, m), 3.14 (1H, d, J=18 Hz), 3.47 (1H, dd, J=18 Hz, J'=6.5 Hz), 5.41 (1H, s, OH), 6.63–6.73 (2H, m, ArH), 6.93–7.00 (1H, m, ArH).

EXAMPLE 2

Preparation of 3-hydroxy-17-deaza-17-allylthionium-17-thiamorphinan 12

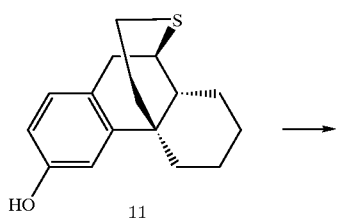

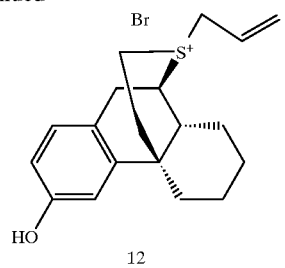

The thiamorphinan 11 (0.10 g) was dissolved in dry acetonitrile (1.5 ml), and to this was added allyl bromide (2 ml). The solution was allowed to stir at room temperature for 72 hours at which time the reaction was diluted with cold diethyl ether causing precipitation. The precipitate was then filtered and washed with cold ether to give the product a white solid. Yield 15% (0.022 g).

¹H NMR (DMSO, 400 MHz, δ in ppm); 1.0–1.65 (9H, m), 2.1–2.25 (2H,m), 3.05–3.1 (2H,m), 3.45–3.55 (1H,m), 3.75–3.8 (0.75H, m), 3.9–3.95 (0.25H, m), 4.15–4.2 (0.67H, d), 4.3–4.38 (1.33H, d), 5.5–6.1 (3H,m) 6.2–7.2 (2H, m, ArH), 7.0–7.09 (1H, m, ArH), 9.31 (0.33H, s, ArOH), 9.325 (0.67H, s, ArOH)

In a similar manner, the analogous methyl-thionium compound, 3-hydroxy-17-deaza-17-methylthionium-17-thiamorphinan 17 was prepared using methyl bromide in place of allyl bromide.

EXAMPLE 3

Preparation of 3-hydroxy-17-deaza-17-dimethylallylthionium-17-thiamorphinan 13

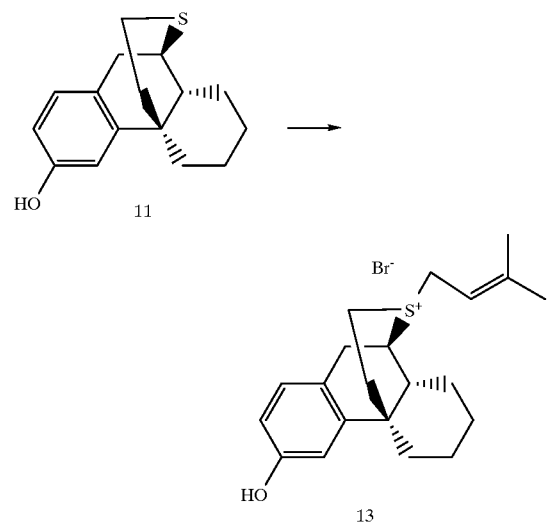

The thiamorphinan 11 (0.050 g) was dissolved dry acetonitrile (10 ml), and 4-bromo-2-methyl-2-butene (0.65 ml, 30 eq) was added. The solution was allowed to stir at room temperature for 72 hours at which time the reaction was diluted with cold diethyl ether causing precipitation. The precipitate was then filtered and washed with cold ether to give the product, a white solid. Yield 81% (0.064 g).

¹H NMR (DMSO, 400 MHz, δ in ppm); 1.0–1.8 (9H, m), 1.8 (6H, s), 2.15–2.3 (2H, m), 2.9–3.15 (2H, m), 3.5 (2H, dd), 3.75 (1H, d), 5.28–5.35 (1H, t), 6.65–7.02 (3H, m, ArH), 9.31 (1H, s, ArOH).

EXAMPLE 4

Preparation of 3-hydroxy-17-deaza-17-phenethylthionium-17-thiamorphinan 14

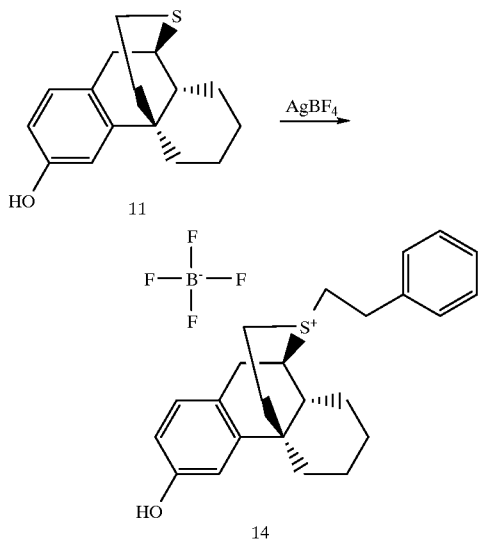

The thiamorphinan 11 (0.150 g) was dissolved in phenethyl iodide (0.72 ml), and to this was added silver tetrafluoroborate (0.0118 g, 1.0 eq). The solution was allowed to stir at room temperature for 72 hours at which time the reaction was diluted with methylene chloride and filtered. The filtrate was then evaporated, the residue re-dissolved in ethanol/water (1:1), extracted with ether and the aqueous phase lyophilized to give a white solid. Yield 3.2%.

EXAMPLE 5

Preparation of Resolved α (15) and β (16) Conformers of Sulfallorphan

α-sulfallorphan (compound 15) and β-sulfallorphan (compound 16) and were prepared according to the procedures described by Belleau et al in Can. J. Chem., 1986, 64:110, incorporated herein by reference. Briefly, the α and β conformers were isolated by converting the mixture to a picrate derivative and then fractionally crystallizing.

EXAMPLE 6

Inhibition of NMDA-induced Convulsion

Male Swiss Webster mice [(SW) fBR] 20–25 g (Canadian Breading Farms St. Constant, Quebec), were coinjected intracerebroventricullarly (i.c.v.) with various doses of test compound and NMDA (1 and 2 nmol; Sigma Chemical Co., St. Louis, Mo.) in total volume of 10 μl. The mice were observed for 30 min after injection for signs of convulsion and death. The convulsive response to NMDA was within 5 minutes of injection, characterized by wild running, popcorn jumping and myoclonic seizures (i.e. repetitive movements involving all limbs simultaneously, usually accompanied by loss of righting reflex). A minimum of 15 animals were used in each treatment group. The number of mice convulsing in each group was recorded. The dose producing convulsions in 50% of the mice ($CD_{50}$) was calculated by the method of Litchfield and Wilcoxon ("Manual and Pharmacological Calculations with Computer Programs", 2nd ed., Springer, N.Y., 1987). Results of the inhibition study, summarized in table 1, show that compounds of the invention exhibit greater anti-convulsive activity than typical NMDA antagonists.

TABLE I

| | $CD_{50}$ (nmol/mouse) | |
|---|---|---|
| COMPOUND | (1 nmol NMDA) | (2 nmol NMDA) |
| dextrorphan | 0.55 | >100 |
| dextrallorphan | 2.68 | 43.2 |
| levorphanol | 0.21 | >200 |
| levallorphan | 1.06 | >20 |
| example 2  12 | 0.07 | — |
| example 3  13 | 0.19 | — |
| example 4  14 | 0.99 | — |
| 17 | 0.02 | — |
| α-sulfallorphan 15 | 0.476 | 1.52 |
| β-sulfallorphan 16 | 0.015 | 0.28 |

EXAMPLE 7

Inhibition of AMPA, Kainic Acid and Bicuculline-induced Convulsions

Male Swiss Webster mice [(SW) fBR]20–25 g, were coinjected intracerebroventricullarly (i.c.v.) with various doses of test compounds, α- and β-sulfallorphan, with AMPA (0.25–2.0) nmol; Research Biochemical Inc.) kainic acid (0.25–0.75 nmol; Sigma Chemical Co.) and biculline (1–10 nmol; Research Biochemical Inc.) in total volume of 10 μl. The mice were observed for 30 min after injection for signs of convulsion and death. The convulsive response to the AMPA, kainic acid and biculline was within 5 minutes of injection, characterized by wild running, popcorn jumping and myoclonic seizures (i.e. repetitive movements involving all limbs simultaneously, usually accompanied by loss of righting reflex). A minimum of 15 animals were used in each treatment group. The number of mice convulsing in each group was recorded. The dose producing convulsions in 50% of the mice ($CD_{50}$) was calculated by the method of Litchfield and Wilcoxon. $LD_{50}$, the dose producing mortality in 50% of the mice, was determined by Fisher's exect test. The results for both α- and β-sulfallorphan are summarized below in tables II and III.

TABLE II

| Convulsant (nmol/mouse) | β-sulfallorphan 16 (nmol/mouse) | $CD_{50}$ (nmol/mouse) | $LD_{50}$ (nmol/mouse) |
|---|---|---|---|
| AMPA | 0 | 0.34 | 2.51 |
| (0.25–5) | 0.4 | 0.29 | none |
| kainic acid | 0 | 0.40 | none |
| (0.25–0.72) | 0.4 | 0.39 | none |
| bicuculline | 0 | 2.48 | 13.40 |
| (1–10) | 0.4 | 3.12 | none | note: none means no mortality observed at dose tested

TABLE III

| Convulsant (nmol/mouse) | α-sulfallorphan 15 (nmol/mouse) | CD$_{50}$ (nmol/mouse) | LD$_{50}$ (nmol/mouse) |
| --- | --- | --- | --- |
| AMPA | 0 | 0.34 | 2.51 |
| (0.25–5) | 1 | 0.26 | 5.24* |
| kainic acid | 0 | 0.40 | none |
| (0.25–0.72) | 1 | 0.39 | none |
| bicuculline | 0 | 2.48 | 13.40 |
| (1–10) | 1 | 4.44 | 12.69 | note: none means no mortality observed at dose tested
*significance at $P \leq 0.05$

EXAMPLE 8

Locomotion and Falling Behavior

Mice were placed individually in observation cages for a 60 minute habituation period, injected i.c.v. with the different compounds and observed from 15 to 30 min. after injection. Locomotion and falling behavior were assessed according to the procedure of Koek and Colpaert (J. Pharm. Exp. Ther., 1990, 252:349). For each mouse the presence of locomotion (locomotion with all four legs moving for at least 15 seconds) and falling behavior (falling from rearing or standing position backward or to the side) was recorded. Statistical significance of drug-induced changes in the occurrence of a particular behavior was tested by the method of Fray et al (., 1980, 69:253). The results summarized in table IV show that thionium compounds of the invention exhibit less side effects such as locomotion and falling behavior than typical NMDA antagonists. In particular α-sulfallorphan exhibited neither effect at any dose tested. β-Sulfallorphan showed less locomotion than dextromethorphan and required greater amount to exhibit a significant effect.

TABLE IV

| Compound | min. Dose for locomotion (nmol/mouse) | min. dose for falling (nmol/mouse) |
| --- | --- | --- |
| dextromethorphan | 0.10 (30) | 0.20 (27) |
| MK-801 | 0.25 (30) | 1.50 (50) |
| α-sulfallorphan 15 | no effect | no effect |
| β-sulfallorphan 16 | 1.25 (20) | no effect | note: numbers in parenthesis indicate the % mice showing significant effect.

EXAMPLE 9

Rotarod Test

The rotarod treadmill for mice (model 7600, UGO Basile, Italy) was used to assess the motor effects of the test compounds. The method used was similar to the procedure described by Dunham and Miya (J. Am. Pharmac. Assoc., 1957, 46:208). The apparatus consisted of a rod with a diameter of 2.5 cm which was suspended horizontally 50 cm above a plain working area. The rod was turned at a speed of 8 revolutions per min. Circular perspex separators were placed at intervals along the rod so that five animals could be tested at the same time. Before administering any compound, all tested mice were placed on the turning rod for 1 min on two consecutive days. Mice that fell from the rod during this test were excluded. The test compounds were administered i.c.v. and the % of mice showing motor effects was monitored. The results illustrated in table V indicate that α-sulfallorphan (30 nmol/mouse) exhibits no significant motor effects while the NMDA antagonist dextrorphan (60 nmol/mouse) induces a significant rise in motor effect.

TABLE V

| Compound | Max. % mice showing motor effect* |
| --- | --- |
| dextrorphan | 60 |
| α-sulfallorphan 15 | 8 |
| β-sulfallorphan 16 | 20 |
| example 3 13 | 0 |
| example 4 14 | 20 |
| 17 | 60 |

*$P \leq 0.05$ as compared with control.

We claim:

1. A method of inhibiting excitotoxicity in a mammal comprising administering to said mammal an excitotoxicity inhibiting amount of a compound of formula (I):

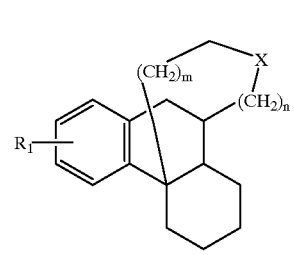

(I)

wherein

R$_1$ is hydrogen, halogen, hydroxyl, N(R$_3$)$_2$, carboxyl, C$_{1-4}$alkyl, C$_{1-4}$alkoxy, C$_{1-4}$alkoxy-carbonyl, C$_{1-4}$acyl, C$_{1-4}$acyloxy, mercapto, C$_{1-4}$alkylthio or a saturated or unsaturated, 5 or 6-member carbocyclic or heterocyclic ring optionally substituted with halogen, hydroxyl, N(R$_3$)$_2$, carboxyl, C$_{1-4}$alkyl, C$_{1-4}$alkoxy or C$_{1-4}$alkoxy-carbonyl;

X is S, SO, SO$_2$ or S$^+$(R$_2$);

R$_2$ is C$_{1-6}$alkyl, C$_{2-6}$alkenyl or C$_{2-6}$alkynyl groups, optionally interrupted with one or more heteroatom and optionally substituted with R$_1$;

R$_3$ is independently H or C$_{1-3}$alkyl;

m is an integer from 0 to 3; and n is an integer from 0 to 2.

2. The method according to claim 1, wherein said excitotoxicity is mediated by the overstimulation of the NMDA receptor complex.

3. The method according to claim 2, wherein said excitotoxicity is mediated by excessive in vivo levels of excitatory amino acids.

4. The method according to claim 3, wherein said excitatory amino acid is NMDA.

5. The method according to claim 4, wherein said excitatory amino acid is glutamic acid.

6. The method according to claim 1, wherein said compound is selected from:

3-hydroxy-17-deaza-17-thiamorphinan 11;

3-hydroxy-17-deaza-17-allylthionium-17-thiamorphinan 12;

3-hydroxy-17-deaza-17-dimethylallylthionium-17-thiamorphinan 13;

3-hydroxy-17-deaza-17-phenethylthionium-17-thiamorphinan 14;

α conformer of 3-hydroxy-17-deaza-17-allylthionium-17-thiamorphinan 15;

β conformer of 3-hydroxy-17-deaza-17-allylthionium-17-thiamorphinan 16; and 3-hydroxy-17-deaza-17-methylthionium-17-thiamorphinan 17.

7. A method of inhibiting a condition in a mammal mediated by overstimulation of the NMDA-receptor complex by administering to said mammal an effective amount of a compound of formula (I)

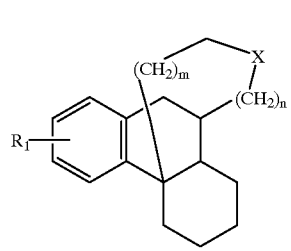

(I)

wherein $R_1$ is hydrogen, halogen, hydroxyl, $N(R_3)_2$, carboxyl, $C_{1-4}$alkyl, $C_{1-4}$alkoxy, $C_{1-4}$alkoxy-carbonyl, $C_{1-4}$acyl, $C_{1-4}$acyloxy, mercapto, $C_{1-4}$alkylthio or a saturated or unsaturated, 5 or 6-member carbocyclic or heterocyclic ring optionally substituted with halogen, hydroxyl, $N(R_3)_2$, carboxyl, $C_{1-4}$alkyl, $C_{1-4}$alkoxy or $C_{1-4}$alkoxy-carbonyl;

X is S, SO, $SO_2$ or $S^+(R_2)$;

$R_2$ is $C_{1-6}$alkyl, $C_{2-6}$alkenyl or $C_{2-6}$alkynyl groups, optionally interrupted with one or more heteroatom and optionally substituted with $R_1$;

$R_3$ is independently H or $C_{1-3}$alkyl;

m is an integer from 0 to 3; and n is an integer from 0 to 2.

8. The method according to claim 7, wherein said condition is ischaemia.

9. The method according to claim 7, wherein said condition is excitatory amino acid induced convulsion.

10. The method according to claim 7, wherein said compound is selected from:

3-hydroxy-17-deaza-17-thiamorphinan 11;

3-hydroxy-17-deaza-17-allylthionium-17-thiamorphinan 12;

3-hydroxy-17-deaza-17-dimethylallylthionium-17-thiamorphinan 13;

3-hydroxy-17-deaza-17-phenethylthionium-17-thiamorphinan 14;

α conformer of 3-hydroxy-17-deaza-17-allylthionium-17-thiamorphinan 15;

β conformer of 3-hydroxy-17-deaza-17-allylthionium-17-thiamorphinan 16; and 3-hydroxy-17-deaza-17-methylthionium-17-thiamorphinan 17.

11. A compound of formula I:

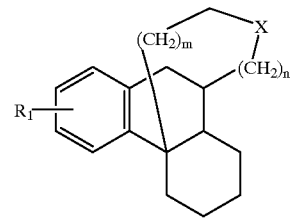

(I)

wherein $R_1$ is hydrogen, halogen, hydroxyl, $N(R_3)_2$, carboxyl, $C_{1-4}$alkyl, $C_{1-4}$alkoxy, $C_{1-4}$alkoxy-carbonyl, $C_{1-4}$acyl, $C_{1-4}$acyloxy, mercapto, $C_{1-4}$alkylthio or a saturated or unsaturated, 5 or 6-member carbocyclic or heterocyclic ring optionally substituted with halogen, hydroxyl, $N(R_3)_2$, carboxyl, $C_{1-4}$alkyl, $C_{1-4}$alkoxy or $C_{1-4}$alkoxy-carbonyl;

X is SO, $SO_2$ or $S^+(R_2)$;

$R_2$ is $C_{1-6}$alkyl, $C_{2-6}$alkenyl or $C_{2-6}$alkynyl groups, optionally interrupted with one or more heteroatom and optionally substituted with $R_1$;

$R_3$ is independently H or $C_{1-3}$alkyl;

m is an integer from 0 to 3; and n is an integer from 0 to 2 with the proviso that when $R_2$ is methyl or allyl then $R_1$ is not H, hydroxy or methoxy.

12. A compound according to claim 11, wherein X is $S^+(R_2)$.

13. A compound according to claim 12, wherein $R_2$ is dimethylallyl.

14. A compound according to claim 12, wherein $R_2$ is phenethyl.

15. A compound according to claim 12, wherein $R_1$ is selected from methoxy and hydroxy.

16. A compound according to claim 12, wherein said compound is in the α conformation.

17. A compound according to claim 12, wherein said compound is in the β conformation.

18. A composition comprising a compound according to claim 11 and a pharmaceutically acceptable carrier.

19. A composition comprising a compound according to claim 11 and a pharmaceutically acceptable carrier wherein said composition is substantially free of the compound in the α conformation.

20. A composition comprising a compound according to claim 11 and a pharmaceutically acceptable carrier wherein said composition is substantially free of the compound in the β conformation.

21. A compound according to claim 11, selected from:

3-hydroxy-17-deaza-17-thiamorphinan 11;

3-hydroxy-17-deaza-17-dimethylallylthionium-17-thiamorphinan 13; and 3-hydroxy-17-deaza-17-phenethylthionium-17-thiamorphinan 14.

* * * * *